United States Patent
Hoshi et al.

(10) Patent No.: US 11,457,641 B2
(45) Date of Patent: Oct. 4, 2022

(54) METHOD FOR PRODUCING FERMENTED MILK FOOD

(71) Applicant: Kabushiki Kaisha Yakult Honsha, Minato-ku (JP)

(72) Inventors: Ryotaro Hoshi, Tokyo (JP); Junki Saito, Tokyo (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 26 days.

(21) Appl. No.: 15/551,471

(22) PCT Filed: Feb. 12, 2016

(86) PCT No.: PCT/JP2016/054079
§ 371 (c)(1),
(2) Date: Aug. 16, 2017

(87) PCT Pub. No.: WO2016/133009
PCT Pub. Date: Aug. 25, 2016

(65) Prior Publication Data
US 2018/0042252 A1 Feb. 15, 2018

(30) Foreign Application Priority Data
Feb. 17, 2015 (JP) .............. JP2015-028221

(51) Int. Cl.
*A23C 9/123* (2006.01)
*A23C 9/13* (2006.01)
*C12N 1/20* (2006.01)

(52) U.S. Cl.
CPC ............ *A23C 9/1234* (2013.01); *A23C 9/13* (2013.01); *A23C 9/1322* (2013.01); *C12N 1/20* (2013.01)

(58) Field of Classification Search
CPC ................. A23C 9/13; A23C 9/1322
See application file for complete search history.

(56) References Cited

U.S. PATENT DOCUMENTS

| 4,087,559 | A | * | 5/1978 | Mutai ............... A23C 9/1234 426/43 |
| 5,545,554 | A | | 8/1996 | Germond et al. |
| 2003/0133921 | A1 | * | 7/2003 | Ohishi ............... A23L 2/02 424/93.45 |
| 2003/0175398 | A1 | * | 9/2003 | Ogasawara ........ A23C 9/1322 426/580 |
| 2004/0013656 | A1 | * | 1/2004 | Matsubara ......... A61K 35/747 424/93.45 |
| 2012/0329135 | A1 | * | 12/2012 | Lopez-Cervantes .... C12P 19/04 435/198 |
| 2013/0266692 | A1 | | 10/2013 | Saito et al. |
| 2015/0056683 | A1 | * | 2/2015 | Hoshi .................. C12N 1/20 435/252.1 |

FOREIGN PATENT DOCUMENTS

| CN | 1156005 | | 8/1997 | |
| CN | 101911973 A | | 12/2010 | |
| CN | 103999935 | | 8/2014 | |
| JP | 10-243776 A | | 9/1998 | |
| JP | 2002-51720 A | | 2/2002 | |
| JP | 2007-28920 A | | 2/2007 | |
| JP | WO 2012/133827 A1 | | 10/2012 | |
| JP | WO 2013/146836 | * | 10/2013 | ............. C12N 1/20 |
| KR | 800000240 | | 4/1980 | |
| WO | WO 98/12931 A1 | | 4/1998 | |
| WO | WO 2011/083776 A1 | | 7/2011 | |
| WO | WO 2012/050094 A1 | | 4/2012 | |
| WO | WO 2012/136833 A1 | | 10/2012 | |
| WO | WO 2013/133313 A1 | | 9/2013 | |
| WO | WO 2014/192905 A1 | | 12/2014 | |

OTHER PUBLICATIONS

Mudai KR 800000240 Apr. 2, 1980 Derwent Translation (Year: 1980).*
KR 820002212 Derwent Abstract (Year: 1984).*
Chronopoulos et al. 2002 Biotechnology Letters vol. 24 Lactic acid fermentation by Lactobacillus casei in free cell form and immobilised on gluten pellets 1233-1236 (Year: 2002).*
International Search Report dated May 17, 2016 in PCT/JP2016/054079 filed Feb. 12, 2016.
Extended European Search Report dated Jul. 3, 2018 in Patent Application No. 16752395.0, 6 pages.
Australian Examination Report dated Sep. 11, 2019, in Patent Application No. 2016220905, 5 pages.
Sutula, J. et al., "The effect of a commercial probiotic drink containing *Lactobacillus casei* strain Shirota on oral health in healthy dentate people", Microbial Ecology in Health and Disease, Retrieved from the internet: https://doi.org/10.3402/mehd.v24i0.21003, vol. 24, No. 21003, 2013, 13 pages.

* cited by examiner

*Primary Examiner* — Felicia C Turner
(74) *Attorney, Agent, or Firm* — Oblon, McClelland, Maier & Neustadt, L.L.P.

(57) ABSTRACT

An object of the present invention is to provide a fermented milk food, in which the viability of lactic acid bacteria during storage is high, the increase in acidity is suppressed, the viable cell count is less reduced, and the flavor is less deteriorated. A method for producing a fermented milk food by which the object was achieved is characterized by inoculating and culturing lactic acid bacteria in a culture medium containing a milk as a main component and supplemented with glucose in such an amount that glucose is substantially entirely assimilated at the time of completion of culturing and fructose in an amount twice or more the amount of glucose in a mass ratio.

16 Claims, No Drawings

METHOD FOR PRODUCING FERMENTED MILK FOOD

TECHNICAL FIELD

The present invention relates to a method for producing a fermented milk food, and particularly relates to a method for producing a fermented milk food, in which the viability of lactic acid bacteria during storage is improved, the increase in acidity is suppressed, and the viable cell count and favorable flavor can be maintained.

BACKGROUND ART

Recently, studies on various bioactive activities of useful microorganisms such as lactic acid bacteria have been conducted, and for example, it has been reported that the lactic acid bacteria improve the intestinal flora and have effects on improvement of bowel movement, enhancement of immunocompetence and the like. With the increase in health consciousness among consumers, a large number of fermented milk foods such as fermented milk drinks and yogurts, with which these useful microorganisms can be taken easily, are sold.

In order to obtain the bioactive effect of lactic acid bacteria, in general, it is considered to be important to take a larger amount of lactic acid bacteria in an alive state, and therefore, a large number of methods of increasing the viability of lactic acid bacteria in fermented milk foods have been studied. However, fermented milk foods containing lactic acid bacteria at a high cell density had a problem that lactic acid bacteria produce organic acids such as lactic acid during storage of the product, and therefore, a sour taste increases to deteriorate the flavor.

In light of this, a method of masking the sour taste by adding sucralose, which is a high intensity sweetener, has been proposed (PTL 1). However, the change in acidity during storage increases with the increase in viable cell count, and therefore, it is difficult to improve the flavor only by using the high intensity sweetener, and a method for fundamentally suppressing the increase in acidity is needed.

On the other hand, with respect to fermented soybean milk, a method of suppressing the increase in acidity during storage by preventing a sugar which can be assimilated by lactic acid bacteria from being brought into a product has been disclosed (PTL 2). However, in the case where a component derived from a milk such as powdered skim milk or powdered whole milk is used, lactose is contained in itself, and therefore, it is impossible to exclude all sugars which can be assimilated by lactic acid bacteria from the product. Therefore, this technique could not be directly applied to fermented milk foods. Further, PTL 2 does not describe the viability of lactic acid bacteria.

CITATION LIST

Patent Literature

PTL 1: JP-A-10-243776
PTL 2: JP-A-2002-51720

SUMMARY OF INVENTION

Technical Problem

An object of the present invention is to provide a technique for producing a fermented milk food, in which the viability of lactic acid bacteria during storage is high, the increase in acidity is suppressed, the viable cell count is less reduced, and the flavor is less deteriorated.

Solution to Problem

The present inventors conducted intensive studies to achieve the above-mentioned object, and as a result, they found that in the production of a fermented milk food, by culturing lactic acid bacteria in a culture medium supplemented with glucose in such an amount that glucose is entirely assimilated at the time of completion of culturing and fructose in an amount twice or more the amount of glucose in a mass ratio, the increase in acidity is suppressed while maintaining the viable cell count during storage of the product, and thus completed the present invention.

That is, the present invention is a method for producing a fermented milk food characterized by inoculating and culturing lactic acid bacteria in a culture medium containing a milk as a main component and supplemented with glucose in such an amount that glucose is substantially entirely assimilated at the time of completion of culturing and fructose in an amount twice or more the amount of glucose in a mass ratio.

Further, the present invention is a fermented milk food obtained by the above-mentioned production method.

Advantageous Effects of Invention

According to the production method of the present invention, the viability of lactic acid bacteria during storage of a fermented milk food can be improved, and also the increase in acidity can be suppressed. Therefore, the fermented milk food of the present invention is a fermented milk food, in which a favorable flavor is maintained, and with which a large amount of lactic acid bacteria having various bioactive activities can be taken in an alive state.

DESCRIPTION OF EMBODIMENTS

The method for producing a fermented milk food of the present invention includes a step of inoculating and culturing lactic acid bacteria in a culture medium containing a milk as a main component (hereinafter, sometimes referred to as "milk culture medium"), thereby obtaining a culture of lactic acid bacteria.

The milk which is the main component of the culture medium is not particularly limited as long as it is a milk itself or a milk product produced using a milk as a raw material, and for example, cow milk, goat milk, sheep milk, powdered whole milk, powdered skim milk, fresh cream, and the like are exemplified, and any of these can be used as the culture medium directly or by dilution as needed. Incidentally, this culture medium may be a culture medium supplemented with a component which is used in a common culture medium for lactic acid bacteria. Examples of such a component include vitamins such as vitamin A, B vitamins, vitamin C, and E vitamins; various peptides; a tea extract; oleic acid; amino acids; and salts of calcium, magnesium, and the like.

The lactic acid bacteria to be inoculated into this milk culture medium are not particularly limited as long as they are lactic acid bacteria generally used in production of foods and they have an ability to assimilate glucose, and examples thereof include *Lactobacillus* bacteria such as *Lactobacillus casei, Lactobacillus gasseri, Lactobacillus acidophilus, Lactobacillus cremoris, Lactobacillus helveticus, Lactoba-* cillus salivarius, Lactobacillus fermentum, Lactobacillus yoghurti, Lactobacillus delbrueckii subsp. bulgaricus, Lactobacillus delbrueckii subsp. delbrueckii, Lactobacillus johnsonii, and Lactobacillus mali; Streptococcus bacteria such as Streptococcus thermophiles; Lactococcus bacteria such as Lactococcus lactis subsp. lactis, Lactococcus lactis subsp. cremoris, Lactococcus plantarum, and Lactococcus raffinolactis; and Enterococcus bacteria such as Enterococcus faecalis and Enterococcus faecium, and among these species of lactic acid bacteria, one species, or two or more species can be used. Among these, lactic acid bacteria capable of assimilating glucose and fructose are preferred. Examples of the lactic acid bacteria having an ability to assimilate glucose and fructose include Lactobacillus bacteria and Streptococcus bacteria, and among these, Lactobacillus casei and the like are preferred, and particularly, Lactobacillus casei YIT9029 (FERM BP-1366, date of deposit: Jan. 12, 1981, the International Patent Organism Depositary, the National Institute of Advanced Industrial Science and Technology (Central 6, 1-1-1, Higashi, Tsukuba-shi, Ibaraki-ken, 305-8566, Japan)) is preferred. Incidentally, the International Patent Organism Depositary was moved to a new address: #120, 2-5-8 Kazusakamatari, Kisarazu-shi, Chiba-ken, 292-0818, Japan on Apr. 1, 2013 with a new name: the International Patent Organism Depositary, the National Institute of Technology and Evaluation.

In the method of the present invention, when culturing the above-mentioned lactic acid bacteria, a culture medium is prepared by adding glucose and fructose as carbohydrates to a milk culture medium. It is necessary to add glucose in such an amount that lactic acid bacteria can grow until a desired viable cell count or acidity is reached at the time of completion of culturing, and also it is necessary to add glucose in such an amount that the added glucose is substantially entirely assimilated at the time of completion of culturing. When setting the amount of glucose which is substantially entirely assimilated at the time of completion of culturing, the addition amount of glucose to the culture medium may be appropriately adjusted by, for example, measuring the residual amount of glucose contained in the culture of lactic acid bacteria cultured until a desired viable cell count or acidity is reached using a colorimetric method or the like. Examples of the colorimetric method include a method in which glucose is phosphorylated by hexokinase (HK) in the presence of adenosine triphosphate (ATP), the formed D-glucose-6-phosphate is subjected to a dehydrogenation reaction using glucose-6-phosphate dehydrogenase (G6PDH) in the presence of a coenzyme $NADP^+$, and an increase in absorbance (at 340 nm) of the formed NADPH is measured using a spectrophotometer, and the measurement can be performed using an existing kit such as F-kit D-glucose/fructose (manufactured by Wako Pure Chemical Industries Ltd.). Incidentally, the amount of glucose which is substantially entirely assimilated at the time of completion of culturing is such an amount that the acidity during storage is not affected even if glucose is brought into the fermented milk food, and specifically, the residual amount in the culture of lactic acid bacteria after completion of culturing is 0.1 mass % or less, preferably 0.01 mass % or less, more preferably 0.001 mass % or less. Incidentally, the "mass %" refers to w/w %.

The addition amount of glucose may be appropriately set according to a desired acidity or viable cell count as described above, however, for example, in the case where Lactobacillus casei is used, it is necessary to add glucose to the culture medium in an amount of about 0.5 to 4 mass %, preferably 1.5 to 2.5 mass % as the amount which ensures a sufficient viable cell count and also allows added glucose to be substantially entirely assimilated at the time of completion of culturing.

On the other hand, it is necessary to add fructose to a milk culture medium in an amount twice or more the addition amount of glucose determined as described above in a mass ratio, and preferably, fructose is added in an amount 2 to 4 times, particularly preferably 2.4 to 4 times the amount of glucose. By adding fructose in an amount twice or more the amount of glucose, the viability of lactic acid bacteria during storage can be improved. On the other hand, when the amount of fructose exceeds 4 times the amount of glucose, the sugar content in the culture of lactic acid bacteria becomes too high, and therefore, the flavor of the fermented milk food is not favorable in some cases. In the case where the production method of the present invention is used, fructose is hardly assimilated by lactic acid bacteria during culturing, and substantially the entire amount of fructose added to the milk culture medium is left in the culture of lactic acid bacteria as it is, and brought into the fermented milk food.

Glucose and fructose are added to the milk culture medium in the above-mentioned addition amounts, and lactic acid bacteria are inoculated into the culture medium, and thereafter, the lactic acid bacteria are cultured until a desired viable cell count or acidity is reached. A culturing condition for lactic acid bacteria is not particularly limited, however, for example, lactic acid bacteria may be inoculated so that the cell count in the milk culture medium is about $1 \times 10^4$ to $1 \times 10^8$ cfu/mL, and cultured under a condition of 30 to 40° C. Further, the culturing may be performed by appropriately selecting a method suitable for culturing the lactic acid bacteria to be used from static culturing, stirring culturing, shaking culturing, aeration culturing, and the like.

It is preferred that the culturing of lactic acid bacteria is performed until the production of acids by the lactic acid bacteria becomes extremely slow and finally becomes apparently constant, and thereafter the culturing is stopped and completed. If the culturing is continued excessively even after the acidity becomes constant, the acidity during storage is increased in some cases, and therefore, the culturing is preferably promptly completed after the acidity becomes constant, and for example, after the increase in acidity per hour drops to less than 0.05, the culturing is completed preferably within 48 hours, more preferably within 24 hours, particularly preferably within 12 hours. In order to stop the culturing, for example, the culture may be cooled to 10° C. or lower, and the culturing may be stopped by predicting the time when the culturing should be stopped and decreasing the culturing temperature in a stepwise manner from the initial culturing temperature to 10° C. or lower. Incidentally, the acidity can be determined as the amount (mL) of 0.1 N NaOH required for increasing the pH of a sample (9 g) to 8.5.

Further, in the culturing, fermentation may be performed by using lactic acid bacteria in combination with another microorganism, for example, bacteria of the genus Bifidobacterium, the genus Bacillus, the genus Acetobacter, the genus Gluconobacter, or the like; yeast of the genus Saccharomyces, the genus Candida, the genus Rhodotorula, the genus Pichia, the genus Schizosaccharomyces, the genus Torula, the genus Zygosaccharomyces, or the like; or filamentous fungi of the genus Aspergillus, the genus Penicillium, the genus Eurotium, the genus Monascus, the genus Mucor, the genus Neurospora, the genus Rhizopus, or the like; however, in order to suppress the increase in acidity during storage, it is preferred to perform fermentation using only lactic acid bacteria.

The thus obtained culture of lactic acid bacteria can be processed into the fermented milk food of the present invention as it is or by mixing with another food material which is generally added to a fermented milk food.

The fermented milk food of the present invention includes not only fermented milks specified by the Ministerial Ordinance on Milk and Milk Products Concerning Compositional Standards, etc., but also drinks such as dairy product lactic acid bacteria drinks and lactic acid bacteria drinks, and viable cell-containing type foods such as kefir and yogurt. Further, examples of the form thereof include hard type, soft type, plain type, sweet type, fruit type, drink type, and frozen type.

In these fermented milk foods, besides the adjustment of the amounts of glucose and fructose to the addition amounts of the present invention, it is possible to blend other various food materials, for example, arbitrary components such as various carbohydrates, a thickener, an emulsifier, and various vitamins in the above-mentioned culture of lactic acid bacteria as needed. Specific examples of the food materials include carbohydrates such as sucrose, palatinose, trehalose, lactose, xylose, and maltose; sugar alcohols such as sorbitol, xylitol, erythritol, lactitol, palatinit, reduced starch syrup, and reduced maltose syrup; high intensity sweeteners such as aspartame, thaumatin, sucralose, acesulfame K, and *stevia*; various thickeners (stabilizers) such as agar, gelatin, carrageenan, Guar gum, xanthan gum, pectin, locust bean gum, gellan gum, carboxymethyl cellulose, soybean polysaccharides, and propylene glycol alginate; emulsifiers such as sucrose fatty acid esters, glycerin fatty acid esters, polyglycerin fatty acid esters, sorbitan fatty acid esters, and lecithin; milk fats such as cream, butter, and sour cream; acidulants such as citric acid, lactic acid, acetic acid, malic acid, tartaric acid, and gluconic acid; various vitamins such as vitamin A, B vitamins, vitamin C, and E vitamins; minerals such as calcium, magnesium, zinc, iron, and manganese; and flavors such as yogurt-type, berry-type, orange-type, quince-type, *perilla*-type, citrus-type, apple-type, mint-type, grape-type, apricot-type, pear-type, custard cream-type, peach-type, melon-type, banana-type, tropical-type, herb-type, black tea-type, and coffee-type flavors. Incidentally, as the carbohydrate, it is more preferred to use a sugar which cannot be assimilated by the lactic acid bacteria to be used.

The thus obtained fermented milk food is a fermented milk food, in which the viability of lactic acid bacteria during storage is improved, the increase in acidity is suppressed, the flavor is less deteriorated, and the viable cell count is less reduced, and with which a large amount of lactic acid bacteria showing various bioactive activities can be taken in an alive state.

Further, the method of the present invention has a characteristic that even if the viable cell count is high, the acidity during storage is less changed as described above, and therefore, in the fermented milk food of the present invention, the viability after storage at 10° C. for 21 days with respect to the viable cell count immediately after production is preferably 85% or more, more preferably 90° or more, and also the viable cell count after storage at 10° C. for 21 days is preferably 1×10/mL or more, more preferably 1.25×10/mL or more.

Further, in the fermented milk food of the present invention, the viability after storage at 10° C. for 30 days with respect to the viable cell count immediately after production is preferably 70% or more, more preferably 80% or more, and also the viable cell count after storage at 10° C. for 30 days is preferably 8×10/mL or more, more preferably 1×10/mL or more.

The viability as used herein refers to a value determined by dividing the viable cell count after storage at 10° C. by the viable cell count immediately after production (on day 0 of storage), and then multiplying the obtained value by 100. Incidentally, the viable cell count of lactic acid bacteria can be measured by, for example, counting colonies of lactic acid bacteria appearing after incubating a sample diluted as appropriate with physiological saline in the BCP medium at 37° C. for 3 days.

Further, the ratio of change in acidity of the fermented milk food of the present invention after storage at 10° C. for 21 days with respect to the acidity immediately after production is preferably 60% or less, more preferably 50% or less, particularly preferably 40% or less. Still further, the ratio of change in acidity of the fermented milk food after storage at 10° C. for 30 days with respect to the acidity immediately after production is preferably 65% or less, more preferably 60% or less, particularly preferably 50% or less. Incidentally, the change in acidity as used herein refers to a difference between the acidity after storage at 10° C. and the acidity immediately after production (on day 0 of storage), and the ratio of change in acidity can be determined by dividing the change in acidity by the acidity immediately after production, and then multiplying the obtained value by 100.

In this manner, according to the production method of the present invention, the viability of lactic acid bacteria during storage of the fermented milk food is improved, and also the increase in acidity is suppressed, and therefore, the production method can be applied to a method for improving the viability of lactic acid bacteria during storage of a fermented milk food or a method for suppressing the increase in acidity during storage of a fermented milk food, each including the same step as the production method of the present invention described above, and these methods are also included in the present invention.

EXAMPLES

Hereinafter, the present invention will be described in detail with reference to Examples. However, the present invention is by no means limited to these Examples.

Example 1

To a 15 mass % powdered skim milk culture medium (containing about 7.5 mass % lactose, acidity: 2), a monosaccharide shown in Table 1 was added and dissolved, and the resulting solution was sterilized at 100° C. for 60 minutes. Into each culture medium, a starter of *Lactobacillus casei* YIT9029 was inoculated in an amount of 0.5 mass % (initial cell count: $7.5 \times 10^7$ cfu/mL), and culturing was started at 37° C. While adjusting the culturing temperature, the culture solution was cooled to 10° C. when the acidity reached 23. Incidentally, the increase in acidity per hour of culturing was 0.03 at the time point 12 hours before the culturing was completed. Incidentally, *Lactobacillus casei* YIT9029 is a lactic acid bacterial strain having an ability to assimilate glucose and fructose. Separately, a syrup was prepared by dissolving the components shown in Table 2 in water. The obtained culture of lactic acid bacteria and the syrup were mixed at a mass ratio of 1:3.1, whereby a drink-type fermented milk food was prepared. The fermented milk food was stored by refrigeration (10° C.), and the acidity and the viable cell count were measured immediately after production (on day 0 of storage) and on day 21 and day 30 of storage by the following measurement methods. Further, also evaluation of the flavor was performed immediately after production (on day 0 of storage) and on day 21 and day 30 of storage in a similar manner.

The actually measured amounts of glucose and fructose contained in the culture of lactic acid bacteria immediately after culturing and in the fermented milk food immediately after production are shown in Table 3. Incidentally, the measurement of glucose and fructose was performed by the following method. The measurement results of acidity and viable cell count are shown in Table 4. The "%" in Tables 1 to 3 denotes mass %.

<Acidity (mL/9 g)>

The acidity was determined as the amount (mL) of 0.1 N NaOH required for increasing the pH of a sample (9 g) to 8.5.

<Viable Cell Count>

The viable cell count was measured by counting colonies appearing after incubating a sample diluted as appropriate with physiological saline in the BCP medium at 37° C. for 3 days.

<Viability>

The viability was determined according to the following formula from the measured viable cell count.

Viability={viable cell count on day 21 or day 30 of storage at 10° C./viable cell count immediately after production (on day 0 of storage)}×100(%)

<Measurement of Glucose and Fructose>

Glucose or fructose was measured using a food analysis reagent F-kit D-glucose/fructose (manufactured by Wako Pure Chemical Industries Ltd.).

<Change in Acidity>

The change in acidity was determined as a difference between the acidity of a sample on day 21 or day 30 of storage at 10° C. and the acidity of the sample immediately after production (on day 0 of storage).

<Ratio of Change in Acidity>

The ratio of change in acidity was determined according to the following formula from the change in acidity.

Ratio of change in acidity={change in acidity/acidity immediately after production (on day 0 of storage)}×100(%)

<Evaluation Criteria for Flavor>

A: The food has a slight sour taste and a favorable flavor.
B: The food has a sour taste, but the sour taste is within the allowable range.
C: The food has a strong sour taste, and it is difficult to swallow the food.

TABLE 1

|  | Comparative Example 1 | Comparative Example 2 | Comparative Example 3 | Comparative Example 4 | Example 1 |
|---|---|---|---|---|---|
| Glucose | 3.7% | 2.0% | 2.0% | 2.0% | 2.0% |
| Fructose | 3.2% | — | 3.2% | 1.7% | 4.9% |
| Mass ratio (Glucose:Fructose) | 1:0.86 | — | 1:1.6 | 1:0.85 | 1:2.45 |

TABLE 2

|  | Comparative Example 1 | Comparative Example 2 | Comparative Example 3 | Comparative Example 4 | Example 1 |
|---|---|---|---|---|---|
| Sucrose |  |  | 18% |  |  |
| Soybean polysaccharides |  |  | 0.4% |  |  |
| Fructose | — | — | — | 1.0% | — |

TABLE 3

|  |  | Comparative Example 1 | Comparative Example 2 | Comparative Example 3 | Comparative Example 4 | Example 1 |
|---|---|---|---|---|---|---|
| Culture of lactic acid bacteria | Glucose | 1.6% | 0% | 0% | 0% | 0% |
|  | Fructose | 3.1% | 0% | 3.1% | 1.7% | 4.8% |
| Fermented milk food | Glucose | 0.4% | 0% | 0% | 0% | 0% |
|  | Fructose | 0.7% | 0% | 0.7% | 1.1% | 1.1% |

TABLE 4

|  |  | Comparative Example 1 | Comparative Example 2 | Comparative Example 3 | Comparative Example 4 | Example 1 |
|---|---|---|---|---|---|---|
| Acidity (mL/9 g) | Day 0 | 6.1 | 6.0 | 6.0 | 6.0 | 6.0 |
|  | Day 21 | 9.2 | 8.0 | 8.1 | 8.4 | 8.1 |
|  | Day 30 | 10.2 | 8.7 | 8.8 | 9.3 | 8.9 |
| Change in acidity | Day 21 | 3.1 | 2.0 | 2.1 | 2.4 | 2.1 |
|  | Day 30 | 4.1 | 2.7 | 2.8 | 3.3 | 2.9 |
| Ratio of change in acidity | Day 21 | 51% | 33% | 35% | 40% | 35% |
|  | Day 30 | 67% | 45% | 47% | 55% | 48% |
| Cell count (×10$^9$/mL) | Day 0 | 2.6 | 1.8 | 2.0 | 1.7 | 1.8 |
|  | Day 21 | 1.7 | 1.3 | 1.5 | 1.4 | 1.8 |
|  | Day 30 | 1.2 | 0.89 | 1.3 | 1.1 | 1.6 |
| Viability | Day 21 | 65% | 72% | 75% | 82% | 100% |
|  | Day 30 | 46% | 49% | 65% | 65% | 89% |

TABLE 4-continued

| | | Comparative Example 1 | Comparative Example 2 | Comparative Example 3 | Comparative Example 4 | Example 1 |
|---|---|---|---|---|---|---|
| Flavor | Day 0 | A | A | A | A | A |
| | Day 21 | B | A | A | A | A |
| | Day 30 | C | A | A | B | A |

In Comparative Example 1 in which glucose was added excessively and brought into the fermented milk food, the increase in acidity was significant and deterioration of the flavor was observed. Further, in Comparative Examples 2 to 4 in which the amount of glucose added to the culture medium was such an amount that glucose was entirely assimilated at the time of completion of culturing, but fructose was not added or the addition amount of fructose was less than twice the amount of glucose, although there was no significant change in the increase in acidity, the viable cell count was reduced during storage in all cases. On the other hand, in the fermented milk food of Example 1 obtained by culturing in the culture medium supplemented with glucose in such an amount that glucose was entirely assimilated at the time of completion of culturing and fructose in an amount twice or more the amount of glucose in a mass ratio, the acidity was less increased, a favorable flavor was maintained, the viable cell count was hardly reduced, and the viability was significantly high. In Comparative Example 4, fructose was blended in the syrup and the content of fructose in the fermented milk food was set equal to that in Example 1, however, the viability was reduced as compared with that in Example 1, and therefore, it was demonstrated that fructose is required to be present in an amount twice or more the amount of glucose in the culture medium when culturing.

INDUSTRIAL APPLICABILITY

According to the method of the present invention, a fermented milk food in which the viable cell count is less reduced and the acidity is less changed also during storage can be obtained. Therefore, the method is useful as a method for producing a fermented milk food, in which the flavor and the viable cell count can be stably maintained, and with which a large amount of lactic acid bacteria having various bioactive effects can be taken in an alive state.

The invention claimed is:

1. A method for producing a fermented milk food, the method comprising:
inoculating lactic acid bacteria into a culture medium and culturing thereof, wherein the lactic acid bacteria are *Lactobacillus casei* YIT9029 (FERM BP-1366),
wherein the culture medium comprises a milk as a main component and is supplemented with glucose in an amount from 1.5 to 2.5 mass % and fructose in an amount twice or more an amount of glucose in a mass ratio, and
culturing until the amount of glucose in the culture medium at the time of completion of culturing is 0.001 mass % or less wherein the only carbohydrates added to the culture medium for culturing are glucose and fructose, and wherein the viability of the fermented milk food after storage at 10° C. for 21 days with respect to the viable cell count immediately after production is at least 85%.

2. The method of claim 1, wherein the amount of fructose in the culture medium is 2 to 4 times the amount of glucose in the culture medium in a mass ratio.

3. The method of claim 1, wherein the amount of fructose in the culture medium is 2.4 to 4 times the amount of glucose in the culture medium in a mass ratio.

4. The method of claim 1, wherein the viability of the fermented milk food after storage at 10° C. for 21 days with respect to the viable cell count immediately after production is 90% or more.

5. The method of claim 1, wherein the viability of the fermented milk food after storage at 10° C. for 21 days with respect to the viable cell count immediately after production is $1 \times 10^9$/mL or more.

6. The method of claim 1, wherein the viability of the fermented milk food after storage at 10° C. for 21 days with respect to the viable cell count immediately after production is $1.25 \times 10^9$/mL or more.

7. The method of claim 1, wherein the viability of the fermented milk food after storage at 10° C. for 30 days with respect to the viable cell count immediately after production is 70% or more.

8. The method of claim 1, wherein the viability of the fermented milk food after storage at 10° C. for 30 days with respect to the viable cell count immediately after production is 80% or more.

9. The method of claim 1, wherein the viability of the fermented milk food after storage at 10° C. for 30 days with respect to the viable cell count immediately after production is $8 \times 10^8$/mL or more.

10. The method of claim 1, wherein the viability of the fermented milk food after storage at 10° C. for 30 days with respect to the viable cell count immediately after production is $1 \times 10^9$/mL or more.

11. The method of claim 1, wherein a ratio of change in acidity of the fermented milk food after storage at 10° C. for 21 days with respect to an acidity immediately after production is 60% or less.

12. The method of claim 1, wherein a ratio of change in acidity of the fermented milk food after storage at 10° C. for 21 days with respect to an acidity immediately after production is 50% or less.

13. The method of claim 1, wherein a ratio of change in acidity of the fermented milk food after storage at 10° C. for 21 days with respect to an acidity immediately after production is 40% or less.

14. The method of claim 1, wherein a ratio of change in acidity of the fermented milk food after storage at 10° C. for 30 days with respect to an acidity immediately after production is 65% or less.

15. The method of claim 1, wherein a ratio of change in acidity of the fermented milk food after storage at 10° C. for 30 days with respect to an acidity immediately after production is 60% or less.

16. The method of claim 1, wherein a ratio of change in acidity of the fermented milk food after storage at 10° C. for 30 days with respect to an acidity immediately after production is 50% or less.

* * * * *